(12) United States Patent
Haar et al.

(10) Patent No.: US 9,089,293 B2
(45) Date of Patent: Jul. 28, 2015

(54) TEST ELEMENT FOR ANALYZING A BODY FLUID

(75) Inventors: Hans-Peter Haar, Wiesloch (DE); Joachim Hoenes, Zwingenberg (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 173 days.

(21) Appl. No.: 13/351,496

(22) Filed: Jan. 17, 2012

(65) Prior Publication Data
US 2013/0060114 A1 Mar. 7, 2013

Related U.S. Application Data

(63) Continuation of application No. PCT/EP2010/004748, filed on Aug. 3, 2010.

(30) Foreign Application Priority Data

Aug. 13, 2009 (EP) .................................. 09010434

(51) Int. Cl.
  *G01N 33/48* (2006.01)
  *A61B 5/145* (2006.01)

(52) U.S. Cl.
  CPC ..... *A61B 5/14532* (2013.01); *A61B 2562/0295* (2013.01)

(58) Field of Classification Search
  CPC .................... A61B 5/14532; A61B 2562/0295
  USPC .............. 422/401, 410, 412, 425, 82.05, 520; 436/63, 265
  See application file for complete search history.

(56) References Cited

U.S. PATENT DOCUMENTS

| 3,630,957 A | 12/1971 | Rey et al. |
| 4,452,887 A | 6/1984 | Kitajima et al. |
| 5,846,837 A | 12/1998 | Thym et al. |

(Continued)

FOREIGN PATENT DOCUMENTS

| CN | 1176389 A | 3/1998 |
| DE | 1 598 153 A1 | 4/1970 |

(Continued)

OTHER PUBLICATIONS

Hönes, J. et al, "The Technology Behind Glucose Meters: Test Strips", Diabetes Technology & Therapeutics, 2008, Supplement 1, pp. 10 to 26.

(Continued)

*Primary Examiner* — Jill Warden
*Assistant Examiner* — Dwayne K Handy
(74) *Attorney, Agent, or Firm* — Woodard, Emhardt, Moriarty, McNett & Henry LLP

(57) ABSTRACT

A test element includes a puncture element and a test panel. The puncture element has a tip positioned at one end for generating a wound in a body part. A capillary structure extends from the tip to the test panel and has a fluid connection to the tip. The test panel contains at least a part of a reagent system and is positioned in the test element adjacent to a part of the capillary structure of the puncture element so that body fluid penetrating into the capillary structure contacts a liquid entry side of the test panel. The test panel comprises a transparent support layer and a test layer applied to the support layer by coating. The side of the test panel facing away from the support layer forms its liquid entry side, which faces toward the capillary structure.

12 Claims, 12 Drawing Sheets

(56) References Cited

U.S. PATENT DOCUMENTS

| | | |
|---|---|---|
| 6,036,919 A | 3/2000 | Thym et al. |
| 2003/0018282 A1 | 1/2003 | Effenhauser et al. |
| 2008/0108910 A1 | 5/2008 | Hein et al. |
| 2008/0249435 A1 | 10/2008 | Haar et al. |

FOREIGN PATENT DOCUMENTS

| | | |
|---|---|---|
| EP | 1 360 931 A1 | 11/2003 |
| EP | 1 360 933 A1 | 11/2003 |
| EP | 1 269 173 B1 | 8/2005 |
| WO | WO 01/72220 A1 | 10/2001 |
| WO | WO 03/009759 A1 | 2/2003 |
| WO | WO 2005/084546 A2 | 9/2005 |
| WO | WO 2006/105968 A1 | 10/2006 |
| WO | WO 2007/045412 A1 | 4/2007 |

OTHER PUBLICATIONS

International Patent Application PCT/EP2010/004748 (published as WO 2011/018172 A1) International Search Report mailed Dec. 30, 2010.

International Patent Application PCT/EP2010/004748 (published as WO 2011/018172 A1) International Preliminary Report on Patentability mailed Feb. 16, 2012.

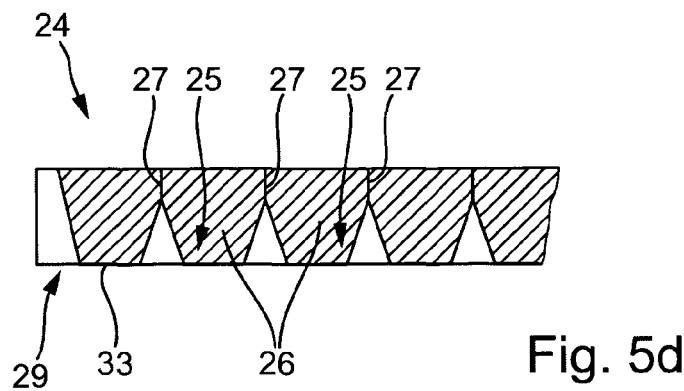
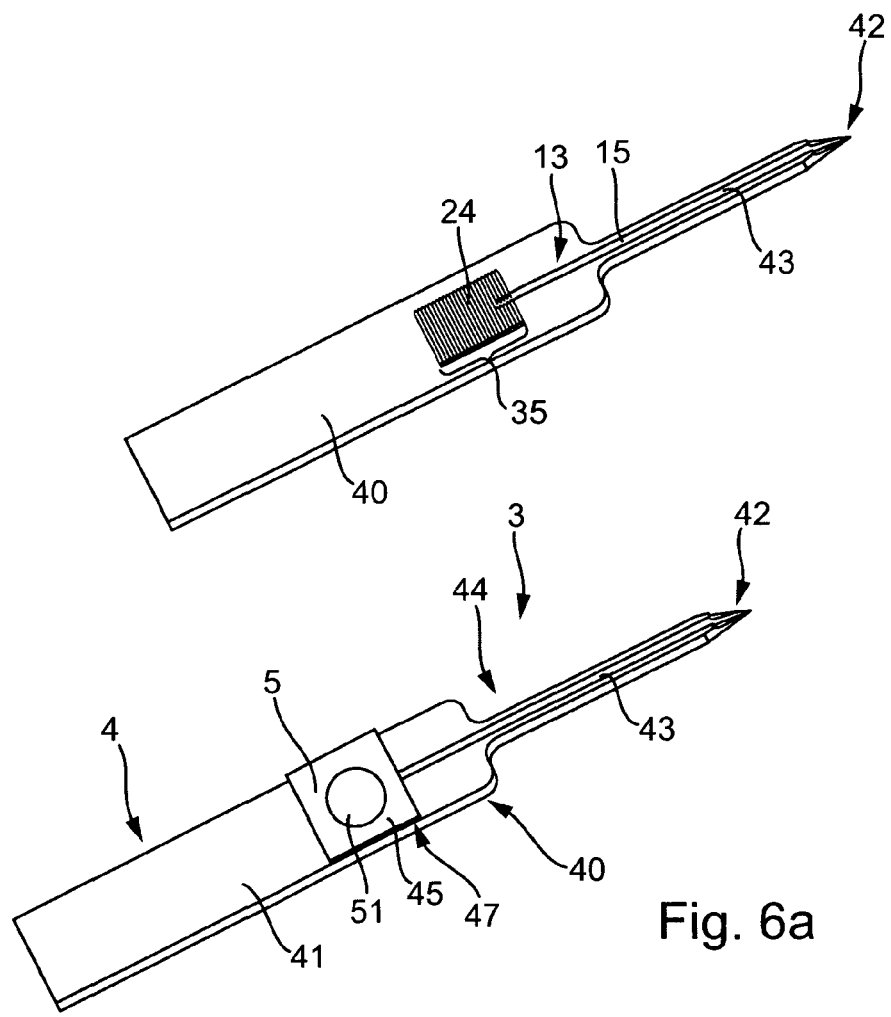
Fig. 5d
Fig. 6a

TEST ELEMENT FOR ANALYZING A BODY FLUID

CROSS-REFERENCE TO RELATED APPLICATION

This application is a continuation of International Application No. PCT/EP2010/004748 filed Aug. 3, 2010, which claims the benefit of European Application No. 09010434.0 filed Aug. 13, 2009, the entire disclosures of which are hereby incorporated by reference.

BACKGROUND

The invention relates to a test element for generating a puncture wound in a body part, for receiving a body fluid from the body part, and for analyzing the body fluid for an analyte contained therein. A method for producing the test element and an analysis system, which includes a test element according to the invention and a specially adapted evaluation device capable of evaluating it, are also the object of the invention.

Such test elements and analysis systems are primarily used for medical analyses. They is are common in numerous variants for the quantitative and qualitative determination of different analytes. Systems for determining the glucose concentration in the blood of diabetics have particularly great medical and economic significance. The invention is particularly suitable for such systems. However, it is not restricted thereto. Another important analyte is cholesterol, for example.

The invention is particularly directed to applications in which the analysis is performed by the patient himself, in order to monitor his health status ("home monitoring"). Simple handling is particularly important in this case. In addition, the evaluation devices must be as small, light, and robust as possible.

The sample required for the analysis is typically obtained by a puncture in the finger or in another body part. The sample liquid is blood and/or interstitial liquid, blood being referred to hereafter without restriction of the generality. In the analysis systems which are still currently predominantly typical, separate instruments are used for the sample acquisition and the analysis, namely a lancet device for generating a wound in a body part, from which blood exits, and analysis elements, for example, in the form of test strips, which are manually brought into contact with the blood exiting from the wound and subsequently evaluated by means of a device associated with the analysis system. This requires multiple handling steps: puncture in the finger, manipulation of the skin surface to encourage the blood exit, contacting the test strip with the blood droplet, and evaluation by means of the device. These handling steps are not only time-consuming and unpleasant, but rather also difficult to perform for many patients, who are typically older and/or impaired by illness.

In order to overcome these problems, analysis systems have been proposed, in which all steps required for the performance of the analysis, from the puncture in the finger up to the display of the analytical result, run completely automatically, without the user having to perform further handling steps after the puncture. Such systems are also designated as "G&M-systems" in the English-language literature, because they allow the sample to be obtained ("G" for "get") and the analytical value to be measured ("M"). Most G&M-systems operate with test elements which have both a puncture element and also an element necessary for the performance of the analysis as integral components. The two components of the test elements (puncture element and analysis element) are typically already assembled into a test element at the producer. However, there are also G&M-systems in which the analysis element and the puncture element are first brought is together in the device in such a manner that a contact is produced between both elements, which allows the transfer of sample liquid from the puncture element to the analysis element and which is designated as "fluid contact".

G&M-systems are described, for example, in the following publications:
(1) WO 01/72220
(2) WO 03/009759
(3) EP 1 360 931 A1
(4) EP 1 360 933 A1
(5) WO 2005/084546
(6) WO 2006/105968
(7) WO 2007/045412

The function of the test systems is decisively influenced by the properties of the test elements used therein. They are to meet an array of difficult and partially contradictory requirements. On the one hand, a high analysis precision is to be achieved. On the other hand, the design is to be as simple as possible and is to allow cost-effective manufacturing. In order to house as many test elements as possible in a device, they are to be as small as possible. A requirement for rapid and reliable analysis is that only a very small sample volume, typically less than 1 µL, is necessary. Finally, the test elements and the associated evaluation devices must be robust enough to ensure reliable function in everyday operation.

SUMMARY

On this basis, the invention is based on the technical problem of providing a test element and an associated test system, which have improved properties with respect to the requirements explained above.

This technical problem is solved by a test element for generating a puncture wound in a body part, for receiving a body fluid sample from the body part, and for analysis by means of a reagent system, whose reaction with an analyte contained in the body fluid results in a change of an optically measurable measuring variable on the test element, wherein the measuring variable is characteristic for the desired analytical result. The test element comprises a puncture element and a test panel, which contains at least one part of the reagent system, the puncture element having a tip positioned on one end of the puncture element for generating a wound in the body part and a capillary structure, which has a fluid connection to the area of the tip in such a manner that after the piercing of the tip of the puncture element into the skin, body fluid penetrates into the capillary structure. The puncture element and the test panel can be positioned relative to one is another in a liquid transfer position so that the test panel is in fluid contact with a part of the capillary structure of the puncture element, wherein body fluid which has penetrated into the capillary structure can be transferred to the test panel. The test panel comprises a transparent support layer and a test layer applied to the support layer by coating. The side of the test layer facing away from the support layer forms its liquid entry side, which faces toward the capillary structure in the liquid transfer position. In the liquid transfer position, the liquid entry side of the test layer therefore immediately and directly adjoins the capillary structure. The liquid transfer from the liquid holding structure, which is formed by the capillary structure, into the test layer occurs directly, without mediation by a third party, in particular without a further structural element located between the capillary structure and the test layer.

The puncture element preferably has an oblong shape, one end of the puncture element being formed having the tip capable of piercing into a body part. The tip is preferably located at a point, at which the lateral surfaces of the oblong puncture element run together, the lateral surfaces ending at the tip being able to have additional sharpened edges. During usage, the front end of the puncture element in the piercing direction pierces into the skin, beginning with the tip. The body fluid then penetrates into the capillary structure and is transported further therein up to the part of the puncture element at which the transfer to the test panel occurs and which is also designated as the liquid transfer area. The penetration of the liquid does not have to occur directly at the tip. Embodiments are even possible in which the tip itself is closed and the capillary structure has an opening behind the tip for the penetration of the body fluid. The part of the puncture element which penetrates into the skin and on which the body fluid enters the capillary structure is also designated hereafter as the tip area or area of the tip of the puncture element. The capillary structure extends in the puncture element from the tip area to the liquid transfer area and therefore allows body fluid to penetrate into the capillary structure after the piercing of the puncture element into the body part and to be transported from the area of the tip to the liquid transfer area. The liquid transfer area of the capillary structure can partially or completely overlap with the area of the tip or is located in an area of the puncture element located distal to the area of the tip.

In the simplest case—as in most of the puncture elements known from the prior art—the capillary structure is a simple channel. According to a preferred embodiment, which will be explained in greater detail hereafter, the capillary structure includes a two-dimensional matrix is structure having a plurality of cells. In general, any formation of the puncture element (as part of the test element), through which the sample liquid, driven by capillary forces, is transported in the puncture element to the liquid transfer area is suitable as a capillary structure. The capillary structure can be implemented over at least a part of its length as grooved or semi-open or also as an at least partially closed channel. The liquid transfer area can be at the end of the capillary structure (e.g., at the end of the grooves or the at least partially closed channel) or in an accessible area, i.e., suitable for the liquid transfer, of the capillary structure between the beginning of the capillary structure (in the area of the tip of the puncture element) and the end of the capillary structure (e.g., in the surroundings of a semi-open grooved structure or an open area of the partially closed channel). In order to ensure the required capillary action, the capillary structure typically consists of a hydrophilic or hydrophilized material.

The test element does not already have to be assembled during the production so that its components puncture element and test panel are located in the liquid transfer position. The liquid transfer from the puncture element to the test layer of the test panel thus does not have to occur readily, in particular not without a relative movement of these elements to one another, as soon as a sufficient quantity of body fluid has penetrated into the capillary structure of the puncture element. Rather, the invention also comprises embodiments in which the test panel and the capillary structure of the puncture element are spatially separated after the production of the test element and are only brought into the liquid transfer position, in which they are in fluid contact with one another, in the analysis device. The puncture element and the test panel can also be associated with separate parts of the test element, which (for example, in the form of a puncture element magazine and an analysis magazine) are inserted into the analysis device. The term "test element" is therefore generally to be understood so that it comprises any packaging in which a puncture element and a test panel can be brought into a liquid transfer position, in which they are in fluid contact with one another. Designs consisting of two partial elements are also possible, if the partial elements are implemented for mutual use in an analysis device. Designs are also possible in which the test panel is fixed on the puncture element in such a manner that the fluid contact exists permanently, i.e., a liquid transfer occurs without a relative movement of both components of the test element, as soon as a sufficient quantity of body fluid has penetrated into the capillary structure of the puncture element.

The analysis is performed by means of a reagent system, which typically consists of is multiple reagents and auxiliary materials, which are integrated in the test element and whose reaction with an analyte contained in the body fluid results in a change of a measuring variable, which is measurable on the test element and which is characteristic for the desired analytical result.

More specific details may be taken from the relevant literature. An overview is given, for example, in the article by J. Hones et al "The Technology Behind Glucose Meters: Test Strips", in Diabetes Technology & Therapeutics, 2008, Supplement 1, pp 10 to 26.

The invention is especially directed to so-called optical analysis elements and systems, in which the change of the test element which is characteristic for the analysis is optically measurable. In optical test elements, the reaction typically results in the change of the color of a layer or surface which is a component of the test element and is designated as a detection layer or detection surface. The color change of the detection layer is measured photometrically. In addition to these "colorimetric" test systems, other optically analyzable test systems are also known, for example, systems in which the measuring variable is a fluorescence signal. The invention generally relates to analysis systems in which the analysis is based on the measurement of a measuring variable optically measurable on the test element, the result of the optical measurement being characteristic for the desired analytical result. Reference is made hereafter to color changes as an example of optically measurable measuring variables without restriction of the generality.

Known optical analysis elements have a support structure, which typically consists of plastic and is usually implemented as narrow, oblong plastic strips ("test strips"). A partial area of the test element in which at least a part of the reagent is localized is designated as a test panel (English: "chemistry pad"). The test panel or chemistry pad can consist of one or more layers, which are in fluid contact with one another and typically run parallel to one another.

Reagent-containing layers of the test panel often consist in typical analysis elements of an absorbent porous layer material (for example, paper, nonwoven material, or a plastic membrane), the reagents being integrated into the pores of the layer. The reagents are introduced into the pores of the layer material during the production of the test layer and are provided therein in soluble form or a form which is bound to the solid phase (or example, by covalent bonding). However, the porous layer forms a solid carrier matrix for the reagents, which is also maintained when the sample liquid penetrates into the matrix and dissolves the reagents. Therefore, this test is layer type can also be designated as a matrix test layer. The aqueous sample liquid is thus absorbed by the porous layer material in this test layer type and thus first brought into contact with the reagents.

Another known test panel type is used in the invention, in which a test layer is applied to a suitable carrier material by coating ("coated test layer"). Such a test layer is also designated hereafter as a CTL layer. To produce a CTL layer, which is also designated as a "test film", the reagents are mixed with a binder or thickener, in order to form a viscous coating mass. After the coating and drying, a thin film is formed on the transparent carrier material. The thickener or binder is therefore also designated as a "film former". The CTL layer is applied (coated) on the transparent and nonporous carrier, without film former or reagents penetrating into the carrier material. The CTL layer must thus be implemented so that upon contact with the aqueous sample liquid, the required reaction for the analysis of the analyte, which is contained in the sample liquid, with the reagents contained in the CTL layer occurs. In order to ensure this, a preferred CTL layer is at least partially soluble and/or swellable. A characteristic feature of such a CTL layer is that, in contrast to the mentioned matrix test layers, it does not have a porous structure, which is permanently solid even after the penetration of the aqueous sample liquid. In order to nonetheless offer a liquid retaining structure for such test panels, network structures or nonwoven materials are used in the prior art, into which the sample liquid can enter and which, as an additional element of the test panel adjoining the CTL layer, provide a liquid column having a defined height and a defined volume. In contrast to the prior art, test panels according to the invention do not have an additional liquid retaining structure or liquid retention structure (of a liquid-resistant layer material). The liquid column of the sample liquid having a defined height and a defined volume, which is directly and immediately in contact with the CTL layer in the liquid transfer position, is provided according to the invention by the capillary structure of the puncture element.

Enzymatic reagent systems are suitable in particular for the invention. They contain an enzyme which reacts specifically with the analyte. In the case of glucose analysis, for example, glucose dehydrogenase (GDH) is used as the enzyme, PQQ-dependent GDH being used particularly preferably in the context of the invention, which is also designated as Gluc-DOR (glucose dye oxidoreductase). The reaction between glucose and enzyme results in a further reaction of a coloration reagent (indicator), which is connected to a color change. The reagent is system preferably contains further reaction components, in particular a mediator, which makes the electron transfer, which is connected to the reaction, from the enzyme to the indicator easier and thus allows a more rapid analysis. This is also explained in greater detail in the relevant literature, for example, in the cited publication of J. Hones et al.

In the test element according to the invention, the test panel comprises a transparent support layer and a test layer (CTL layer), which is applied to this support layer by coating, without an additional liquid retention structure. According to the invention, the liquid retention structure is provided by the puncture element in the liquid transfer position. The test panel is oriented in the test element so that the side of the CTL layer facing away from the support layer forms the liquid entry side and that this side faces toward the capillary structure of the puncture element in the liquid transfer position. Therefore a direct and immediate contact between the body fluid provided in the capillary structure of the puncture element and the CTL layer can occur in the liquid transfer position. The CTL layer can consist of multiple partial layers. It preferably includes two partial layers, a first partial layer coated on the support layer being a reaction layer which contains at least a part of the reagents of the reagent system, and a second partial layer coated on the reaction layer being an opaque light blocking layer. It contains a pigment (for example, TiO2), which substantially prevents the passage of light through the light blocking layer. The grain size of the pigment is preferably dimensioned so that erythrocytes cannot pass or can only pass to a minor extent through the light blocking layer.

During the analysis, the sample liquid is transported through the capillary structure to the liquid transfer area. If the puncture element and the test panel are located in the liquid transfer position, the sample liquid penetrates (perpendicular to the test panel plane) into the adjacent test layer and dissolves the reagents contained therein, so that the provided reactions of the reagent system with the analyte occur. This results in a color change in the test layer. Because of concentration gradients between test layer and sample liquid, diffusion processes of reactive components of the test layer and reacted components of the test layer (products) in the aqueous sample liquid occur. The optical measurement of the color change is performed (preferably by reflection photometry) through the transparent support layer, preferably at a time at which a quasi-stationary state has resulted in the mentioned diffusion procedures. The detection layer is accordingly formed by the CTL layer, preferably by its reaction layer.

In the preferred embodiment having light blocking layer, interference with the optical is measurement by the red blood pigment hemoglobin contained in the sample is substantially prevented, because the light blocking layer blocks the measuring light and (preferably) simultaneously also at least substantially prevents the passage of erythrocytes from the liquid layer located in the capillary structure into the reaction layer. This method for suppressing the hemoglobin interference in optical tests and more specific details about suitable light blocking layers are known from the relevant literature, for example, U.S. Pat. No. 5,846,837.

In the optical tests which the invention relates to, the coloration reaction which is characteristic for the analysis occurs in localized form in the CTL layer. In the case of the preferred two-layer construction of the CTL layer, the coloration is concentrated in the reaction layer—which is more transparent in comparison to the light blocking layer—which therefore can also be designated as the coloration layer. This effect primarily results because the CTL layer only dissolves partially and slowly upon contact with the aqueous sample liquid. At the time of the measurement, it has a viscous consistency and is localized on the support layer. Accordingly, the coloration occurs in the detection layer and in direct proximity to the transparent support layer.

The advantageous effects thus achieved are clear in the comparison to document (3), EP 1360931 A1. A test element is described therein, which essentially consists of a puncture element having a trough-shaped depression designated as a "matrix area" and a top layer spanning the depression.

In a first embodiment, the top layer is transparent, i.e., nonporous. The reagents of the coloration system ("signal producing system") are introduced into the matrix area of the trough-shaped depression. When the sample liquid penetrates into the trough-shaped depression during the performance of a test, the coloration occurs in the trough-shaped depression and can be observed through the transparent cover layer. A large quantity of reagent and a long reaction time are required for sufficient coloration as a result of the large volume of the trough-shaped depression.

In a second embodiment of document (3), it is provided that the cover layer is porous, and thus nontransparent. The space required for the chemical reaction of the coloration system is provided by the pores of the top layer. The top layer consists of an absorbent porous layer material, in whose pores the reagents are impregnated. It is a matrix test layer in the meaning explained above. The coloration can be observed on the surface of the test layer after the is penetration of the sample liquid and occurrence of the coloration reaction. This procedure is slow and requires a correspondingly long test time. In comparison to the test according to the invention, a greater quantity of reagent must be used to achieve similarly intensive coloration and therefore similar precision of the test.

According to the invention, the reaction and coloration occur spatially highly concentrated primarily in the CTL layer. In this regard, it is particularly advantageous if, according to a preferred embodiment of the invention, at least one component of the reagent system, in particular the enzyme or the mediator, particularly preferably the enzyme, is bound to another component of the test layer, in particular a filler contained in the test layer (i.e., a component of the test layer which does not participate in the reaction). This condition is fulfilled in particular if GlucDOR is used together with a negatively charged component of the CTL layer (e.g., based on sodium-aluminum silicate). The enzyme is strongly positively charged, so that a bond based on electrostatic forces results. However, other bonding mechanisms can also be used, for example, based on a covalent bond with other components of the CTL layer (in particular those which do not participate in the reaction). The diffusion of the relevant component of the reagent system after the penetration of the sample liquid is slowed by this bond and therefore the localization in proximity to the transparent support layer is improved.

This localization of the reaction and coloration is one reason why the optical test methods used in the invention allow highly sensitive tests to be implemented using extremely small sample quantities. The test layer is preferably extremely thin (preferably at most 20 µm) and therefore requires only a very small sample quantity in relation to the surface area of the test layer (preferably at most $0.1\ \mu L/mm^2$, particularly preferably at most $0.05\ \mu L/mm^2$). Through the contact of the aqueous sample liquid with the test layer, swelling and/or dissolving of components of the test layer occurs and therefore diffusion processes of reactive components of the test layer and reacted components of the test layer (products) in the aqueous sample liquid and also—although initially to a lesser extent—in the reverse direction from the sample liquid into the test layer. Nonetheless, the concentration of the reaction participants in the area of the detection surface is high and the coloration is intensive. The optical test according to the invention fundamentally differs in this regard from electrochemical tests, in which the reagents are dissolved inside the reaction chamber (electrode chamber), which is equipped with electrodes, so that the size of the reaction volume is determined by the size of the electrode is chamber.

The larger the sample volume available over the test panel, the longer lasting the diffusion processes between the reactive components of the test layer and the sample liquid. A reproducible measurement of a concentration of an analyte can therefore only occur when both the reaction and also the diffusion processes are in a quasi-stationary state, so that a measuring device provided for the evaluation of a test element according to the invention may be calibrated accordingly. This presumes that the quasi-stationary state of the reaction and the diffusion processes is identical during every measurement. This is ensured, on the one hand, in that the test chemistry of the CTL layer is correspondingly applied reproducibly to the support layer. Since the implementation of a quasi-stationary state of the diffusion processes is dependent on the volume, on the other hand, the height of the liquid column and therefore the volume of the sample liquid above the test panel must be dimensioned so that the volume for the diffusion process is to be considered as infinite. The measurement of the system can then be performed independently of volume.

In the context of the invention, it has been established that in spite of the efforts for the smallest possible sample volume, it is advantageous to construct the test element so that the liquid entry side of the test panel is in contact during the reaction with a liquid layer, whose layer thickness has a minimum value in order to minimize the influence of diffusion processes on the course and the optical measurement of the reaction between the reactants present in the sample liquid and the test chemistry of the test panel, so that the measurement can be performed independently of volume. The dimension of the liquid layer perpendicular to the test panel plane is important in this case. This dimension is also designated hereafter as the liquid column.

The height of the liquid column (i.e., the thickness of the liquid layer) determines the duration of the measuring time for which the test element is implemented in this case. The height of the liquid column is thus to be dimensioned in such a manner that the above-described diffusion processes between the aqueous sample liquid and the components of the reaction layer of the test element only have a negligible influence on the course and the result of the optical measurement. In spite of the efforts toward the smallest possible sample volume and a shortened measuring time, i.e., the time between the first contact of the test panel with the sample liquid and the optical measurement (in the case of a plurality of optical measurements, the last optical measurement), a necessary minimum height of the liquid column must thus be ensured to is achieve the desired independence from diffusion procedures. The required minimum height of the liquid column and therefore also the required volume above the test panel are dependent on the respective test chemistry and the structure and thickness of the CTL layer. For example, the following numeric specifications can be made for this correlation:

The capillary structure is to be implemented so that the layer thickness of the liquid layer, which adjoins the liquid entry side of the test panel and is determined by the capillary structure, is at least 100 µm if the test element is implemented for a measuring time of at most 15 seconds.

The capillary structure is to be implemented so that the layer thickness of the liquid layer, which adjoins the liquid entry side of the test panel and is determined by the capillary structure, is at least 50 µm if the test element is implemented for a measuring time of at most 5 seconds.

The capillary structure is to be implemented so that the layer thickness of the liquid layer, which adjoins the liquid entry side of the test panel and is determined by the capillary structure, is at least 20 µm if the test element is implemented for a measuring time of at most 1 second.

It is thus essential that, in coordination with the test chemistry and structure of the CTL layer, the height of the liquid column is selected as sufficiently great that essentially no change of the measurement results caused by diffusion processes occurs, i.e., the measurement can be performed independently of the volume.

This minimal condition with respect to the liquid column requires an additional volume. Nonetheless, test elements according to the invention can be designed as extremely small, because the required liquid column is not provided in the analysis part of the test element, but rather, in the puncture element. The capillary structure integrated into the puncture element forms a "liquid retention structure", in which the required liquid column is held available in contact with the optical test panel. The fluid is in direct diffusion exchange with the CTL layer and the reagents of the reagent system contained therein. Complete diffusion equilibrium does not necessarily have to occur in this case. It is sufficient if the diffusion exchange occurs in such a manner that a reproducible optical measurement is made possible.

The capillary structure integrated in the puncture element therefore has two functions. On is the one hand, it ensures the transport of the body fluid from the area of the tip of the puncture element to the distal end of the puncture element. On the other hand, it functions as a "liquid retention structure" and ensures that body fluid can be transferred from the capillary structure into the test element, and, at least until the completion of the measurement, a predefined minimum value of the liquid layer thickness is maintained in the area of the wetting and is available on the test panel during the measurement. Therefore, in spite of the occurrence of diffusion procedures between components of the reaction layer of the test panel and the body fluid stored in the capillary structure, the desired measurement precision is achieved. An additional liquid retention structure as in test elements of the prior art is not necessary. This function is instead formed by the puncture element, which is preferably produced from metal.

In the liquid transfer position, the liquid entry side of the test layer directly adjoins the capillary structure. Therefore, a further layer, in particular a liquid retention structure, for example, a network or nonwoven material, is not located between the liquid entry side of the test layer and the capillary structure. The single liquid retention structure of the test element is formed by the capillary structure in the test element, i.e., the liquid in the capillary structure of the test element is in direct diffusion exchange with the CTL layer of the test panel. The CTL layer does not contain any porous components which could be used as a liquid retention structure.

The test panel can have extremely small dimensions both in its surface extension and also in its thickness. It is preferably integrated into the test element so that its supporting element is the puncture element. It therefore fundamentally differs from a complete test strip (or other analysis elements), as was used in earlier designs of a G&M-test element.

Overall, decisive advantages are achieved by the invention:
  The design is simple and cost-effective to produce, as explained in greater detail hereafter.
  In spite of the minimum size of the liquid retention layer, an extremely small construction results overall. This not only results in a small required sample volume, but rather also contributes to a high sensitivity of the test.

The test element according to the invention is implemented so that, at least at a transfer time, the capillary structure of the puncture element approaches the test layer of the test panel in is such a manner that a liquid transfer occurs from the capillary structure (directly) to the test panel. At the transfer time, the test panel is thus located in the liquid transfer position, in which the liquid entry side of the test layer directly adjoins the capillary structure. In particular, an additional liquid retention structure is not provided between the capillary structure of the test element and the test layer. Before or after the transfer time, puncture element and test panel can be located relative to one another in a position in which no liquid transport is possible. However, they must be able to be positioned in such a liquid transfer position.

The liquid retention structure which is absent in the test panel is provided according to the invention by the capillary structure of the puncture element. Since the liquid retention structure must first be present upon transfer of the liquid to the test panel, an approach or contact of puncture element and test panel only at or shortly before the transfer time of the liquid is sufficient. In this embodiment, the element required for the analysis is only completed when the puncture element approaches in such a manner that the capillary structure provides a liquid retention structure for the test panel and blood reaches the test panel from the puncture element.

In a particularly preferred embodiment, the capillary structure of the puncture element comprises a two-dimensional planar matrix structure having a plurality of cells. It extends in particular in the liquid transfer area of the puncture element, in which the fluid contact with the test panel occurs. Each of the cells of the matrix structure has a cavity, the largest dimension of the cell cavities of the matrix structure being less than the average width of the capillary channel of the puncture element. The cell cavities have a defined height perpendicular to the two-dimensional extension of the matrix structure (matrix plane), by which the minimum value of the layer thickness of the liquid layer is ensured.

The cell cavities of the cells have a fluid connection to one another through liquid passages in such a manner that a liquid penetrating into the matrix structure is two-dimensionally distributed to a plurality of cells. The cells are open on a transfer side of the matrix structure, which adjoins the liquid entry side of the test panel. A transfer of the liquid from the matrix structure to the test panel can thus occur.

A structure in which a plurality of cells are positioned adjacent to one another in a matrix plane is designated as a two-dimensional (planar) matrix structure. Cells are preferably provided in a plane only in the spatial direction perpendicular to the matrix plane (which runs parallel to the test panel plane). The planar matrix structure thus has a "height" of one cell. A liquid is transferred from the capillary channel to the test panel therefore only passes one cell height (in the direction transverse to the plane of the matrix).

The planar matrix structure preferably is a fluid connection to the capillary channel and the capillary structure and distributes the liquid flowing from the capillary channel into the matrix structure on a greater width in comparison to the capillary channel, before the liquid contacts the test layer of the test panel. A planar distribution of the liquid occurs in such a manner that the layer thickness of the liquid in the cells has a desired minimum value. In this way, it is ensured that the area of the test panel determined by an optical system is wetted as uniformly as possible.

In the context of the invention, it has been established that a very homogeneous distribution of the liquid is performed using such a cell matrix structure. The capillary structure has the function of a spreading layer. If the matrix structure is constructed like a network, reference is made to a spreading network in technical circles. Spreading is understood in the meaning of the invention as the distribution of a liquid in the matrix plane in such a manner that a predefined minimum value of the liquid layer thickness is maintained in the area of the wetting and is available during the measurement on the test panel. The liquid is preferably distributed in the matrix structure so that a minimum filling height is maintained in all (wetted) cells and a further cell is only filled when the minimum liquid height is exceeded in the other already filled cells.

It has been established in the context of the invention that in particular in the case of small sample volumes (for example, 100 nL or less), the type of the blood distribution to the individual cells of the matrix structure is of particular significance. The individual cells must have a defined minimum liquid thickness, so that the precision of the measurement on the distributed liquid is independent of the blood quantity (volume) or the height of the blood layer. This requirement is reliably fulfilled by the cell matrix structure. The puncture element according to the invention additionally allows very controlled and rapid spreading, so that the test layer is simultaneously or quasi-simultaneously wetted by the filled cells. Wetting which differs greatly with respect to time results in a non negligible error during the measurement. The term "simultaneous" is to be considered as a function of the measuring time. The distribution is considered simultaneous if the liquid is distributed to the cells within one-tenth, preferably within one-twentieth of the measuring time.

In a preferred embodiment, the puncture element having the capillary channel and the matrix structure is produced in one method step. The production is preferably performed by etching and/or by laser cutting.

The method according to the invention for producing a puncture element having a capillary channel and a matrix structure is particularly a photoetching method, in which after the masking using photoresist and exposure, the puncture element having the capillary channel results from the mask structure by means of etching and the matrix structure having a plurality of cells is generated.

In a preferred embodiment, the two-dimensional matrix structure is generated by etching in the same etching procedure as the production of the capillary channel. The laser cutting, which is also preferred, of the planar matrix structure in an additional processing step of laser cutting practically does not increase the production costs of the test element, since the investment costs of the laser are low.

BRIEF DESCRIPTION OF THE DRAWINGS

The invention is explained in greater detail hereafter on the basis of the preferred embodiment shown in the figures. The special features shown therein can be used individually or in combination to provide preferred embodiments of the invention. The embodiments described here do not represent a restriction of the invention defined by the claims. In the figures:

FIGS. 5a to d show two embodiments of a capillary structure as part of the test element according to the invention;

FIGS. 6a to c show alternative embodiments of a test element;

DESCRIPTION OF THE SELECTED EMBODIMENTS

Figure 1:
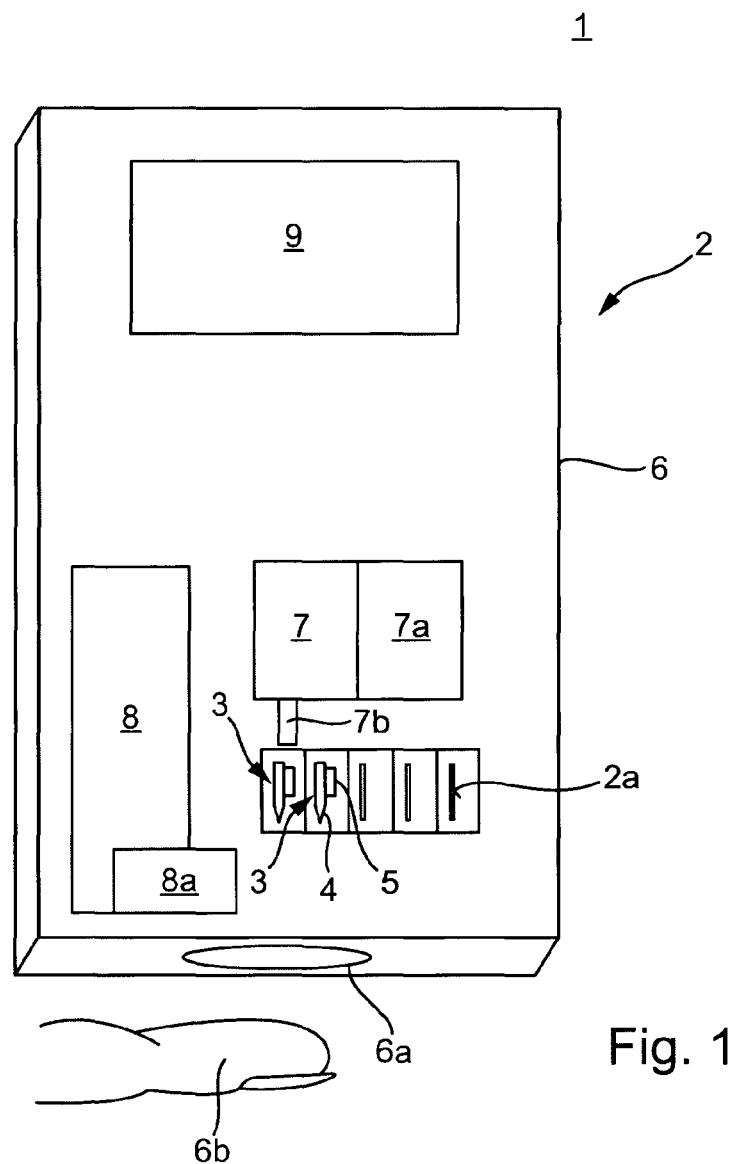
FIG. 1 shows a schematic outline of an analysis device having a plurality of test elements.

FIG. 1 shows an analysis system 1 having an analysis device 2 and a magazine 2a, which is contained in the device 2, having test elements 3. The test elements 3 each comprise one puncture element 4 and one test panel 5.

The analysis device 2 has a housing 6 and a coupling mechanism 7 for coupling to the puncture element 4, in order to move it on a movement path in a piercing direction. The coupling mechanism 7 is coupled to a drive unit 7a, which moves a coupling structure 7b, which can be coupled to the puncture element 4.

A measuring and evaluation unit 8 is used to measure a change of a reagent, which reacts with the body fluid, of the analysis element 5, in order to analyze an analyte of the body fluid. Both a quantitative analysis and also a qualitative analysis can be performed. The glucose content in the blood is preferably studied. In the example shown, the measuring and evaluation unit 8 operates according to a photometric measuring principle and has a lens 8a, which measures the test element 3.

The analysis device 2 comprises an analysis unit (display) 9 for displaying the results of the analysis. The patient or user who operates the analysis device 2 can read off the result directly. Therefore, a "one-step treatment" results for the patient or user of the analysis device 2. He holds the analysis device 2 with a contact opening 6a of the device 2 on his fingertip 6b in such a manner that the puncture element 4 can generate a puncture wound in the fingertip 6b.

Figure 2:
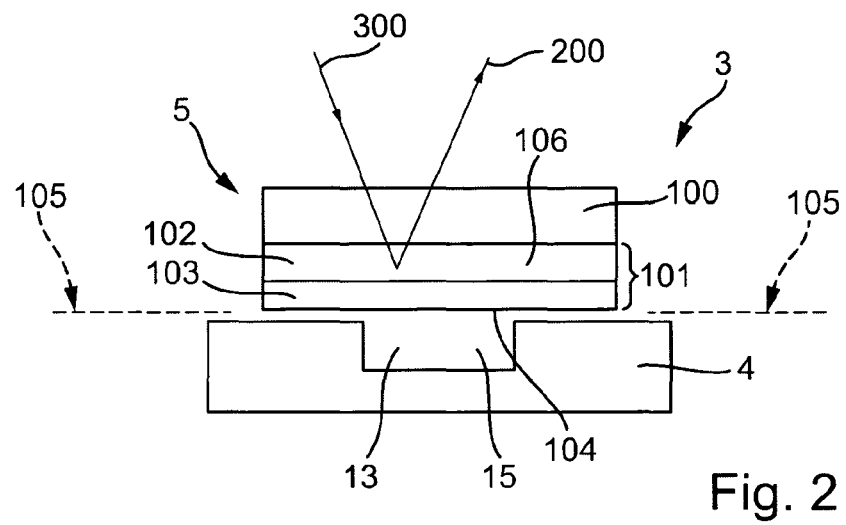
FIG. 2 shows an embodiment of a test element.

FIG. 2 shows a sectional view through a test element 3 according to the invention having a puncture element 4 and a test panel 5. The puncture element 4 has a capillary structure 13, which is formed in the simplest case by a capillary channel 15. Alternatively, the capillary structure 13 comprises a matrix structure, as explained in greater detail hereafter on the basis of FIGS. 4 and 5, for example.

The test panel 5 comprises a transparent, liquid-impermeable support layer 100 and a test layer 101 adjoining the support layer 100, which is coated on the support layer 100. In the present case, the test layer 101 is formed from a reaction layer 102 and a light blocking layer 103, the reaction layer 102 adjoining the transparent support layer 100. The light blocking layer 103 has a liquid entry side 104 on its side facing away from the reaction layer 102, which forms a test panel plane 105. The test panel plane 105 extends perpendicularly to the sectional plane. It adjoins the capillary channel 15 of the puncture element 4.

As mentioned, the test layer 101 having its two partial layers (reaction layer 102 and light blocking layer 103) is preferably implemented so that the erythrocytes are separated by the light blocking layer during the penetration of the sample, so that the red blood color cannot penetrate into the reaction layer to a practically interfering extent. The reaction layer is implemented so that it scatters the light significantly less in the wet state than the light blocking layer. Both layers are preferably produced on the basis of a dispersion or emulsion, the same film former being able to be used, but the use of different film formers also being possible. Furthermore, it is preferable for at least the reaction layer, preferably also the light blocking layer, to contain a swelling agent. The light blocking layer additionally contains a filler which does not participate in the reaction, but makes the penetration of the sample liquid into the layer easier. In the context of the invention, precipitated silicic acid is preferably used for this purpose. The light blocking layer contains a strongly scattering pigment, for example, TiO2. In any case, different fillers or pigments are used in the two layers in such a manner that the reaction layer scatters the light less in the wet state than the light blocking layer. The scattering coefficient of the light blocking layer is preferably at least 10 times as high as the scattering coefficient of the reaction layer.

For reasons of comprehensibility, the size ratios of the test element 3 shown in FIG. 2 do not correspond to the real ratios. In reality, the thickness of the support layer 100 is significantly greater than the thickness of the test layer 101 applied by coating. The support layer thickness is preferably approximately 50 μm to approximately 200 μm. The thickness of the test layer 100 is only a few micrometers, preferably less than 30 μm, particularly preferably less than 20 μm, and very particularly preferably less than 10 μm. The ratio of the thicknesses of the light blocking layer 103 and the reaction layer 102 to one another is preferably in a range from 3:1 to 1:3. The test panel 5 adjoins the puncture element 4 in such a manner and typically contacts it so that the test panel plane 105 is flush with the liquid entry side 104 and with the upper side of the puncture element 4 and the open side of the capillary channel 15. The test panel plane 105 therefore corresponds to the transfer side of the capillary structure 13.

Liquid entering the capillary channel 13 wets the test layer 101, so that liquid penetrates into the test layer 101. An optical measurement of the color change induced by the liquid in the test layer 101 is performed by a light beam 200, which penetrates into the support layer 100 on the side of the support layer 100 facing away from the test layer 101. The light beam 200 is scattered and reflected inside the test layer 101, preferably inside the reaction layer 102 of the test layer 101. The reaction layer 102 is a detection layer 106 in which the color change occurs. The scattering and therefore the light beam reflected from the test element 3, which can be optically evaluated, changes due to the color change occurring during the reaction in the test layer 101. The light blocking layer 103 prevents the light 200 from penetrating into the capillary structure 13 and prevents red blood cells of blood present in the capillary channel, for example, from influencing the optical measurement.

Figure 3A:
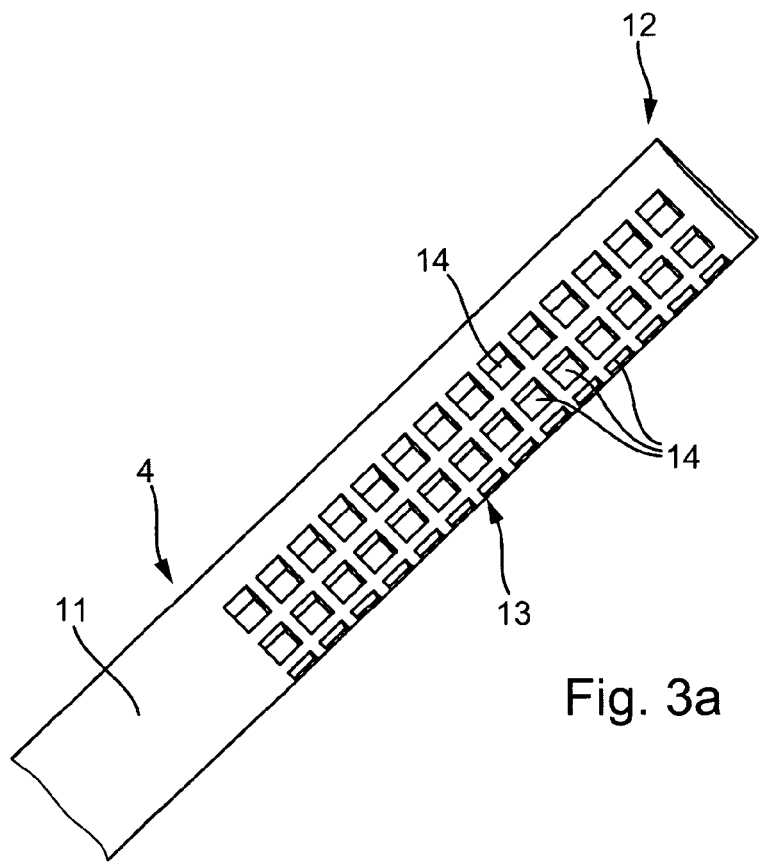
FIGS. 3a to c show detail views of an alternative embodiment of a puncture element having a matrix structure.

FIG. 3a shows a detail of a special embodiment of a puncture element 4, which is a hollow needle 11 having a tip (not shown here). The hollow needle 11 has a capillary structure 13, which, at a remote end 12 of the hollow needle 11 opposite to the tip, comprises a plurality of recesses 14, which are integrated in the outer wall of the hollow needle 11 and are positioned adjacent to one another. The recesses 14 can be square, for example, the dimension of the recesses 14 in the peripheral direction being at most 50 μm, preferably at most 30 μm. The height of the recesses 14, i.e., the dimension in the radial direction of the hollow needle 11, is preferably between 30 μm and 100 μm, preferably at least 50 μm. It is determined by the is material thickness of the hollow needle 11. Since the dimensions of the recesses 14 are smaller than the diameter of the hollow needle 11, the capillary effect in the individual recesses 14 is greater than that of the hollow needle 11. The blood flows out of the needle 11 into the recesses 14 and is distributed uniformly onto a plurality of recesses 14. When a test panel 5, which is preferably curved, corresponding to the hollow needle 11 approaches, the capillary structure 13 forms a liquid retention structure for the test panel 5, which does not have a separate liquid retention structure itself.

Figure 3B:
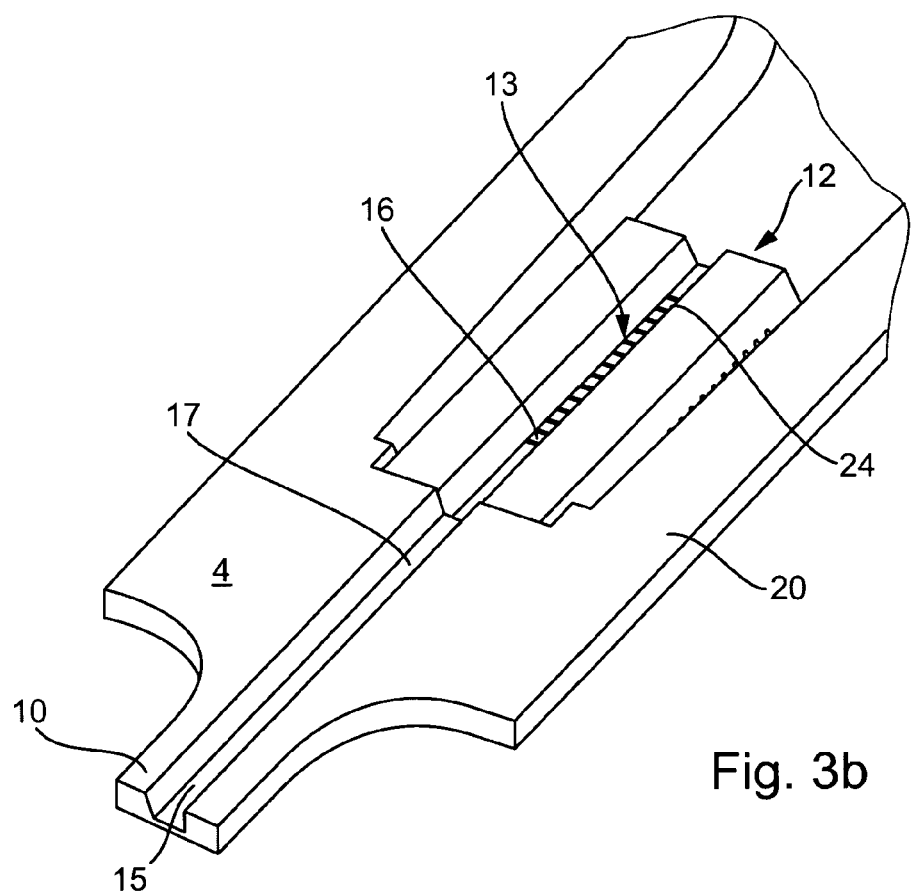
Figure 3C:
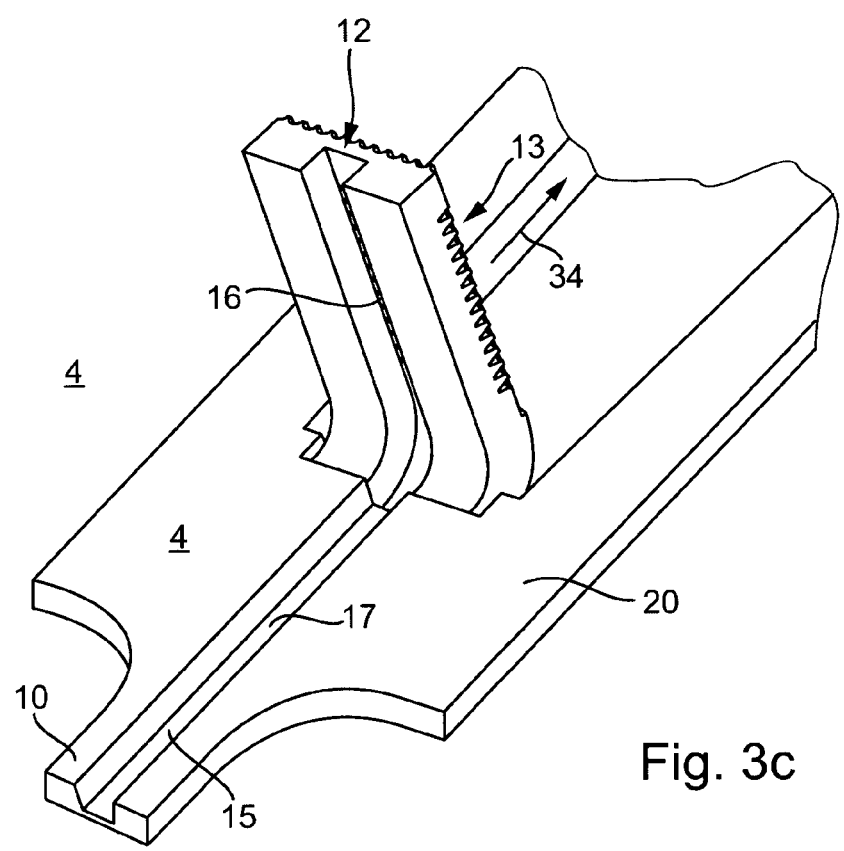

FIGS. 3b and 3c each show a detail of two further embodiments of a puncture element 4 according to the invention. It is implemented as a flat needle element 10 and has a capillary structure 13, which comprises a capillary channel 15 open on one side, which extends away from a tip (not shown here). The capillary channel 15 is open on both sides on its remote end 12, a second opening 16 extending on the floor 17 of the capillary channel 15. In addition, the capillary channel 15 is also open on its end 12. The second opening 16 on the floor 17 is also part of the capillary structure 13 and can be implemented in the form of a network or a matrix structure, for example.

FIG. 3c shows an embodiment in which the remote end 12 of the capillary channel 15 is angled (preferably by 90°). The capillary structure 13 can be moved into fluid contact with the test panel (liquid transfer position) to transfer a sample liquid by a relative movement in the direction of the arrow 34 between the puncture element 4 and a test panel (not shown here). The capillary structure 13 then forms the liquid retention structure of the analysis element.

A further embodiment of a test element 3 according to the invention is shown in FIGS. 4a to 4d, which also has a flat puncture element 4. A needle element 10 is implemented on one end of the puncture element 4. The needle element 10 has a tip 19 on its free end 18 for generating a puncture wound. A capillary channel 15 open on one side extends from the tip 19 in the longitudinal direction of the needle element 10 up into a flat puncture body 20 of the puncture element 4. In an area 21 close to the remote end 12 of the capillary channel 15, the capillary channel 15 has a further recess 16 in its floor 17; it is therefore open on both sides.

The area 21 of the capillary channel 15 which is open on both sides is a section of the capillary channel 15 facing away from the tip 19, which is positioned closer to the remote end 12 than to the tip 19. A capillary structure, in particular a matrix structure 24, which distributes inflowing liquid, is positioned below the area 21. The capillary channel 15 can extend beyond is this section. This has the advantage that blood entering the capillary channel 15 from the tip 19 first flows away via the matrix structure 24, so that a first partial quantity of the blood collects in a section positioned at the remote end 12 of the capillary channel 15. This partial quantity of the blood does not penetrate into the matrix structure 24, since the flow speed inside the capillary channel 15 is so great that the capillary action of the structure 24 is subject to the force exerted by the flow speed. This prevents the first partial quantity of the blood from being analyzed, which can be contaminated by sweat particles, for example. As soon as the blood has reached the free end of the capillary channel 15, the flow speed decreases. The capillary action of the structure 24 now absorbs the blood.

Figure 4A:
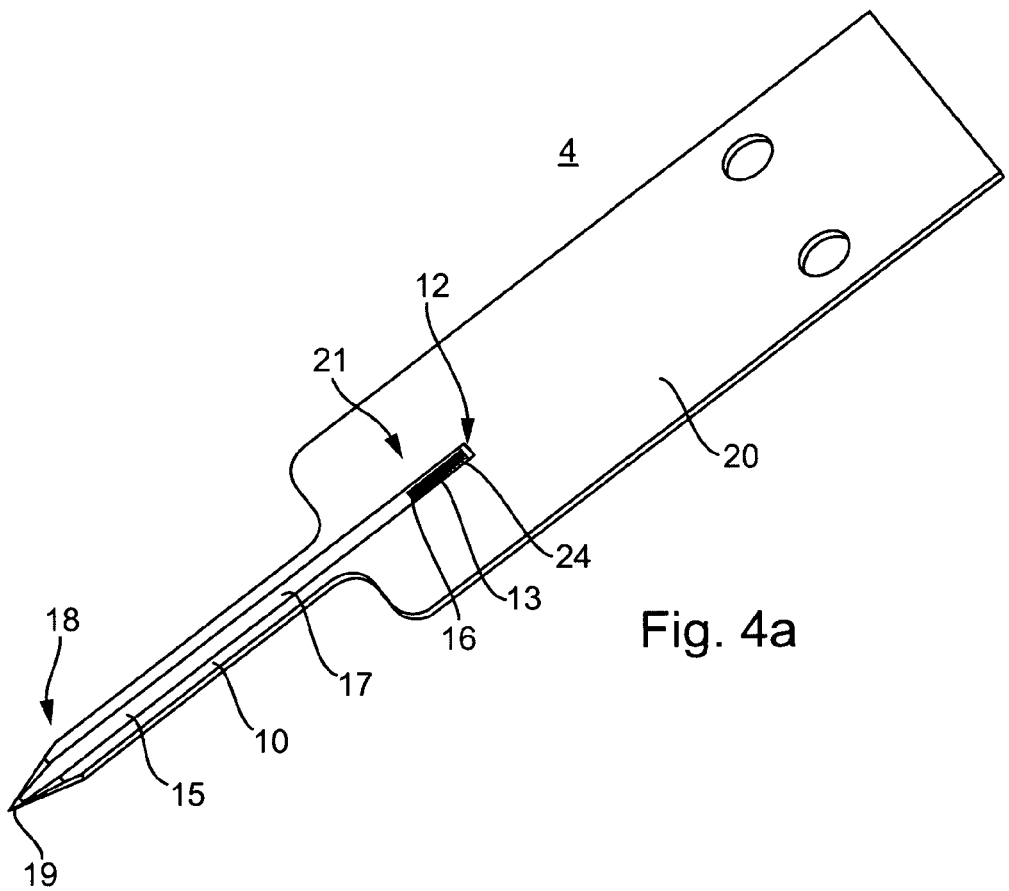
FIGS. 4a to d show a further embodiment of a puncture element.
Figure 4B:
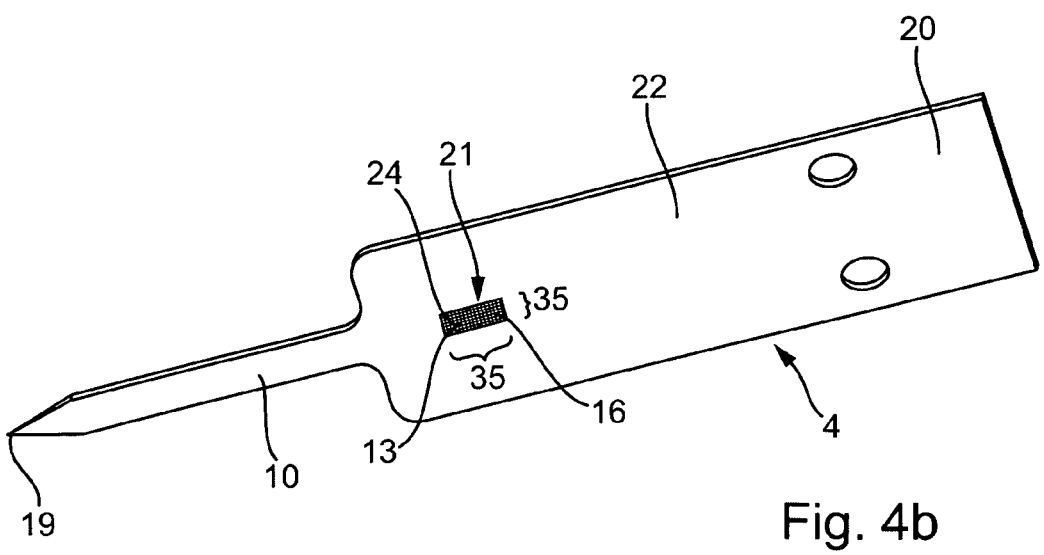

FIG. 4b shows the lower side 22 of the puncture element 4. The capillary structure 13, which is implemented as the matrix structure 24, is positioned in the open area 21. It is preferably integrally connected to the puncture element 4. Puncture element 4 and matrix structure 24 are particularly preferably formed from one element. They are both made of metal. The open area 21 is a liquid transfer area 35, in which the transfer of a liquid from the capillary structure 13 (via the matrix structure 24) to an adjacent test panel 5 (FIG. 4c) occurs.

Figure 4C:
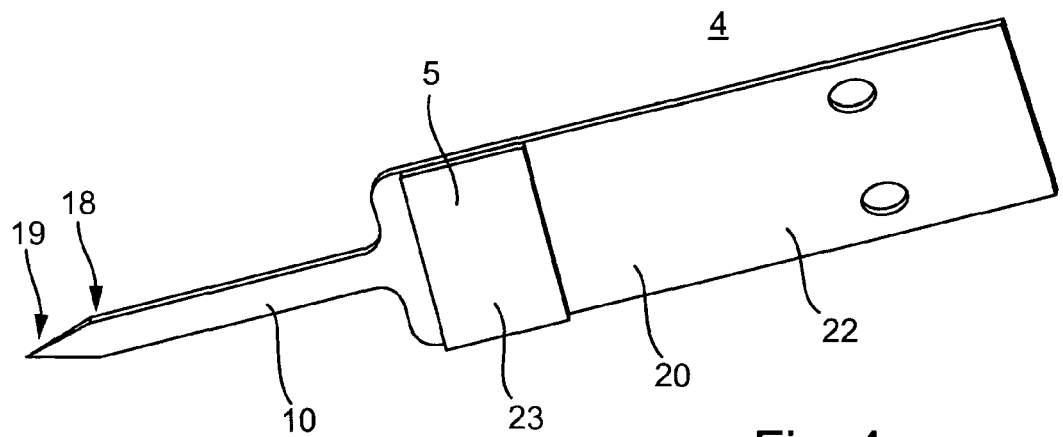
Figure 4D:
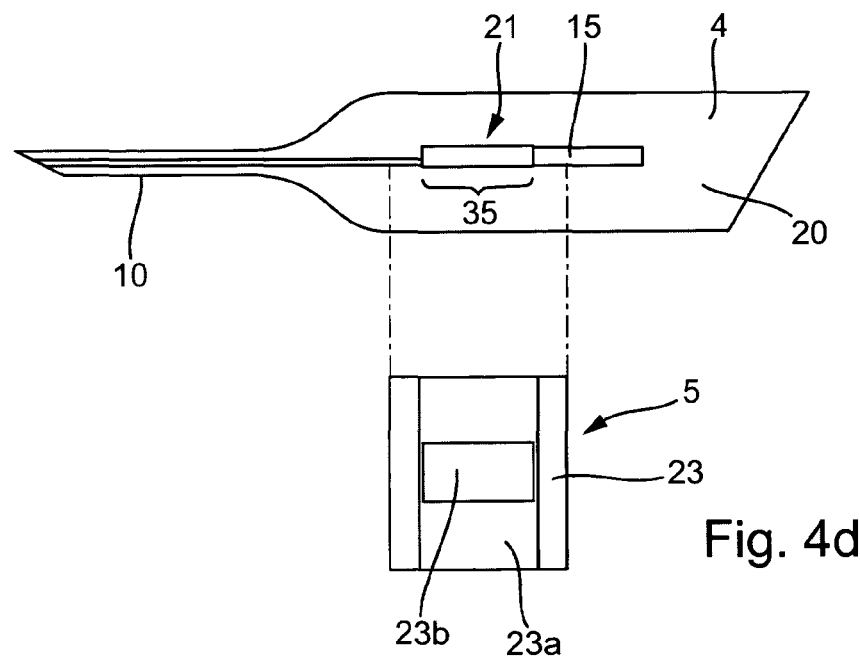

FIG. 4c shows that a test panel 5 is positioned on the lower side 22 of the puncture element 4, the capillary structure 13 being covered by the test panel 5. The test panel 5 comprises a support layer 23 and a test layer 23a having a test zone 23b, FIG. 4d. The test zone 23b is preferably adapted to the open area 21 and the capillary structure 13 positioned therein. The liquid transfer area 35 extends beyond the matrix structure 24 (not shown here). The liquid transfer area 35 is implemented as slightly smaller in this embodiment than the test zone 23b; however, it can also be larger than or the same size as the test zone 23b. In this embodiment, the liquid transfer area 35 at least corresponds to the open area 21.

FIGS. 5a, 5b and 5c, 5d show various embodiments of a two-dimensional matrix structure 24, which can be part of a capillary structure 13 of a test element 3 according to the invention. The two-dimensional matrix structure 24 has a plurality of cells 25, which each have a cell cavity 26, whose greatest dimension is smaller than the average width of the capillary channel of the test element 3. Because of the smaller dimensions of the cells 25, the capillary action of the matrix structure 24 is greater than that of the capillary channel 15, so that liquid flows out of the capillary channel 15 into the matrix structure 24. The occurring capillary force is the essential component, and preferably the exclusive component. The thickness of the liquid is layer and the liquid volume related thereto in the matrix structure 24 is less than the volume which is offered by the liquid channel (capillary channel 15) and is available for a measurement. In this way, the matrix structure 24 is always sufficiently filled and the measurement result is independent of the primary liquid quantity available.

In these preferred embodiments, the cell cavities 26 of the cells 25 have a fluid connection with one another through liquid passages 27 in such a manner that a liquid penetrating into the matrix structure 24 is distributed two-dimensionally to a plurality of cells 25. The cells 25 are open on a transfer side 28 of the matrix structure 24 to transfer the liquid to a test layer of the test panel 5.

Figure 5A:
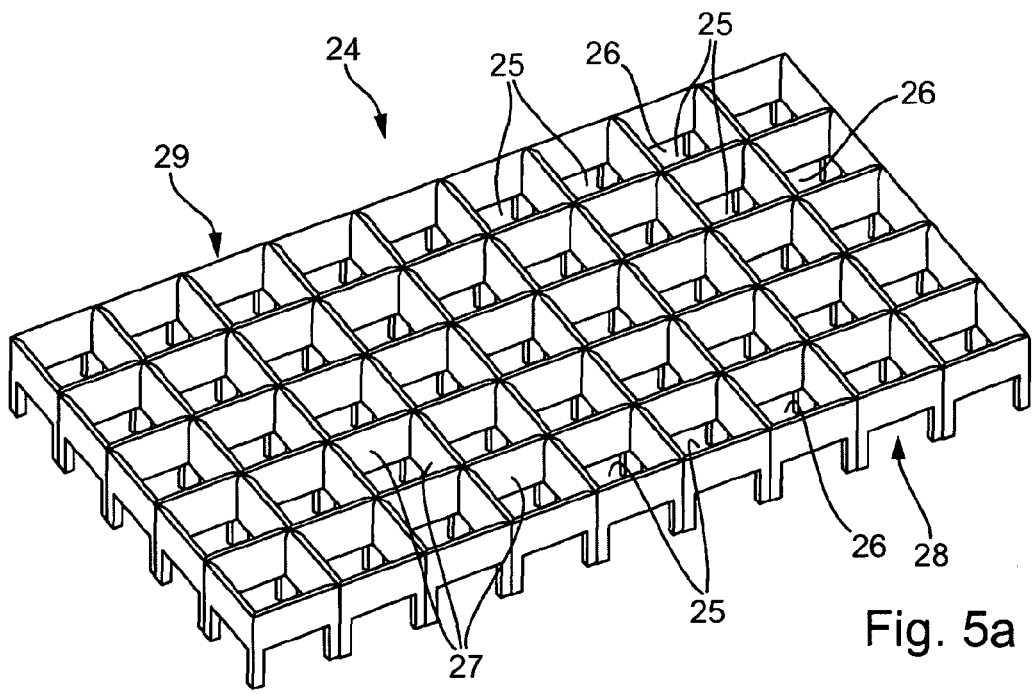

The matrix structure 24 according to FIG. 5a has the form of a grating, which is open on an upper side. The upper side is preferably a liquid entry side 29. The cells 25 have a rectangular cross-section, preferably a square cross-section. The side length of the cells should be 20 to 50 μm. Their thickness is preferably 20 to 100 μm. Of course, they can also assume arbitrary shapes (round).

If the two-dimensional matrix structure 24 is positioned parallel and adjacent to a capillary channel 15 of a puncture element 4, a liquid transfer occurs from the capillary channel 15 to the matrix structure 24. The transfer side 28 of the matrix structure 24, which is implemented as the lower side, is also open, so that the liquid can be transferred into the test panel 5. The liquid is distributed in the matrix structure 24 so that a desired liquid column results in the individual cells 25.

The term two-dimensional (planar) matrix structure is understood as a structure in such a manner that the cells 25 are each only adjacent in one plane (matrix plane). An arrangement of a plurality of cells 25 one over another is not provided.

As shown in FIG. 5a, the matrix structure 24 can be open on both sides. Thus, if the matrix structure 24 is positioned at the end of the capillary channel 15 and the sample liquid flows laterally into the matrix structure 24, a test panel can be positioned both on the lower side (transfer side 28) and also on the upper side of the matrix structure 24. A double measurement for independent control of the measurement result is thus possible. Alternatively, two measurements can also be performed simultaneously, for example, if two different analytes or different parameters are to be determined from only one sample. It has proven to be advantageous if the matrix structure 24 consists of metal, as in FIG. 5a, since the wetting of a is metal structure occurs significantly more rapidly than the wetting of a fabric or nonwoven material.

Figure 5B:
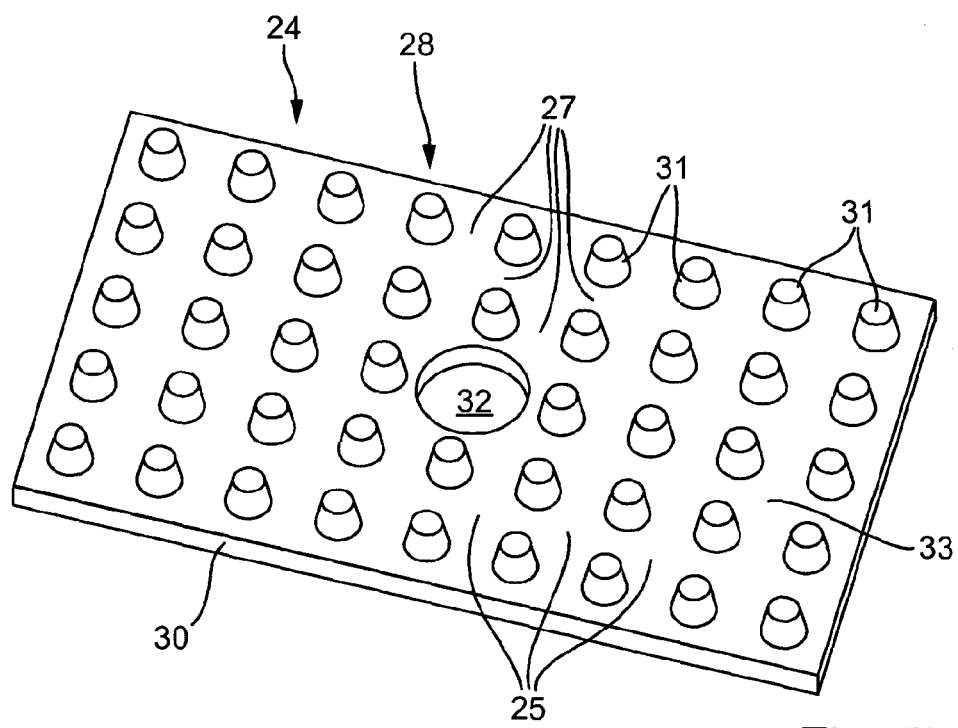

The embodiment of the matrix structure 24 according to FIG. 5b shows a plate-shaped main body 30, on whose lower side a plurality of nubs 31 is positioned. The individual cells 25 of the matrix structure 24 are formed between the nubs 31. The main body 30 has a recess 32 on its upper side, through which the liquid can reach the individual cells 25. A liquid is distributed to a plurality of cells 25, a predefined layer thickness of the liquid (liquid column) resulting in each of the cells 25 filled with liquid and a redistribution to adjacent cells 25 only occurring thereafter. The predefined liquid column is maintained in the first filled cells 25.

The transfer of the liquid from the matrix structure 24 to a test panel 5 adjoining the structure 24 occurs via the open nubby side (transfer side 28) of the matrix structure 24, on which the cells 25 have cell openings 33, through which the liquid exits.

Figure 5C:
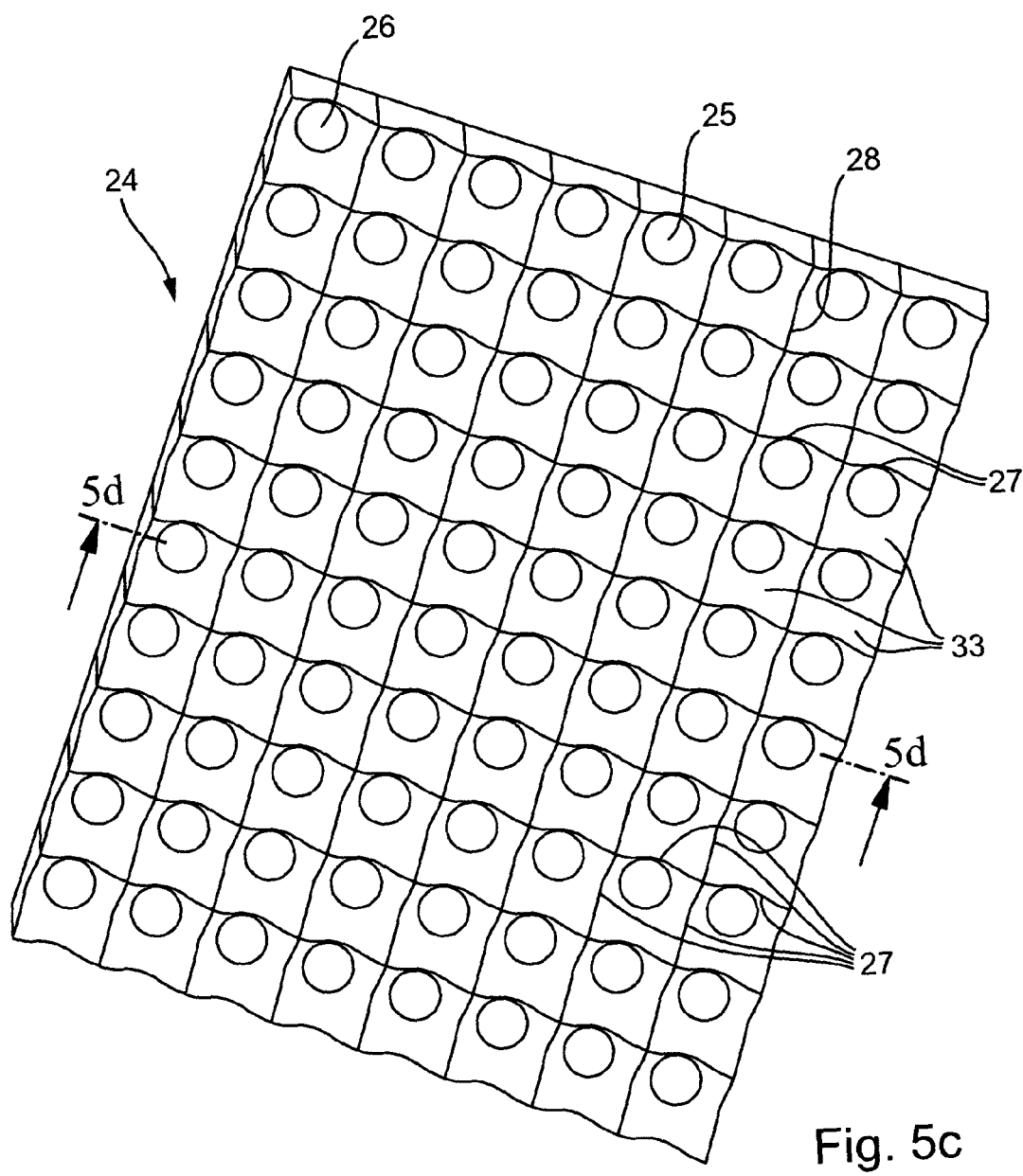

FIGS. 5c and 5d (sectional view) show a further embodiment of a matrix structure 24, whose cells 25 are implemented in such a manner that the cell cavities 26 preferably widen toward the transfer side 28. The cell cavities 26 preferably widen continuously. The matrix structure 24 is open on its upper side (liquid entry side 29) in such a manner that a liquid can penetrate into the individual cells 25. On the lower side (transfer side 28), the cells 25 have cell openings 33 for transferring the liquid to an adjacent test layer. The individual cells 25 have a fluid connection to one another via liquid passages 27 in such a manner that the liquid is distributed to a plurality of cells 25.

In a preferred embodiment, the height of the cells 25 is between 20 μm and 150 μm. The cell height is advantageously between 30 μm and 100 μm. It is preferably at least 50 μm. Such cell heights also allow small liquid volumes of at most 50 mL to be determined. The spreading layer (matrix structure 24) according to FIG. 5c has a size of 320 μm×400 μm, which is calculated from the 80 cells 25 having square cross-section. The cells 25 each have a side edge of 40 μm and a height of 60 μm. Each cell 25 therefore has a net volume of 0.096 mL. The total volume of the matrix structure 24 is approximately 7.7 mL. Since the spreading layer has an effective liquid absorption volume of approximately 60% of the total volume, a volume of approximately 4.5 mL can be received therein. The liquid is distributed to a plurality of cells 25 (preferably to all cells 25) having a sufficient liquid column (at least 50 μm) above the adjoining is test layer, so that the optical measurement is independent of the liquid quantity.

In a preferred embodiment, the matrix structure 24 has at least 20 cells 25, preferably at least 25 cells 25, and particularly preferably at least 50 cells 25. An embodiment in which the matrix structure 24 comprises at least 100 cells 25 is still more preferable.

The large number of cells 25 in combination with thin cell walls, which are very small (cell wall thickness less than 10 μm) in comparison to the dimensions of the cells 25, allows a statistical evaluation during an optical measurement of the matrix structure 24. Since sufficient wetting or coverage of the matrix structure 24 with liquid does not occur at the intersection points of the cell walls of the cells 25, no optical evaluation is possible at these points. It is only ensured by the distribution to a plurality of cells 25 having a sufficient liquid column that a sufficiently large number of cells 25 and the liquid volumes contained therein are incorporated in the optical measurement. With a sufficiently high number of cells 25 (at least 20, preferably at least 50), the influence of the cell walls and the node points can be eliminated by statistical evaluation.

Figure 6B:
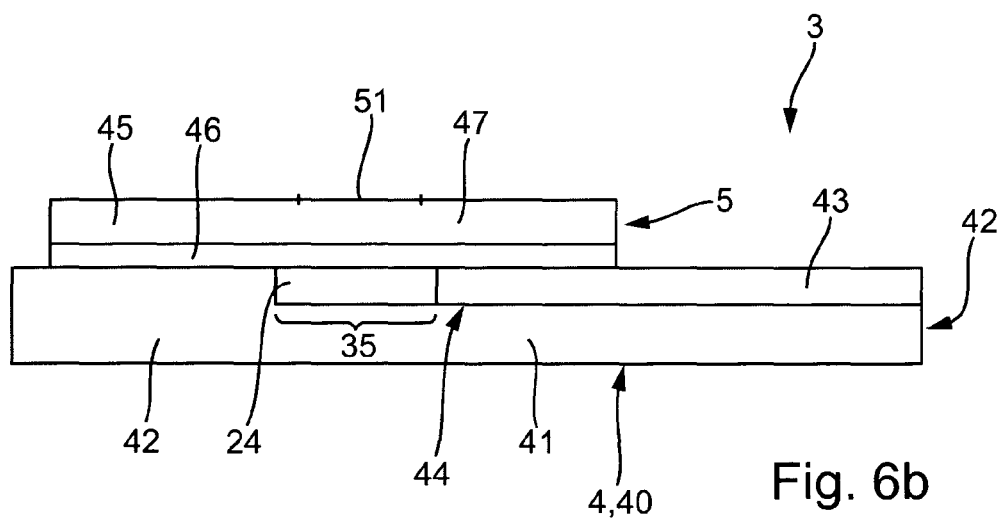
Figure 6C:
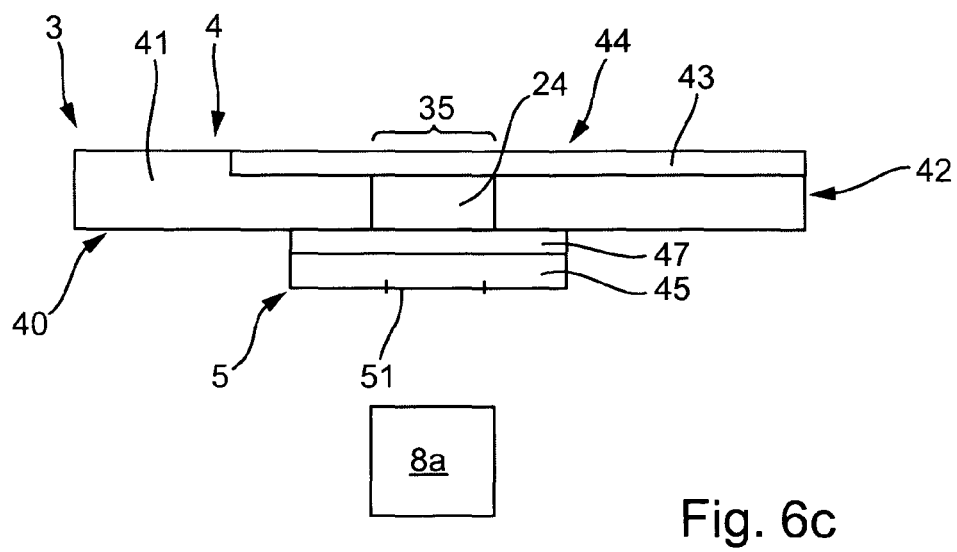

FIGS. 6a to 6c show a test element 3 according to the invention, having a puncture element 4 and a test panel 5. FIG. 6a shows the test element 3 with test panel 5 (bottom) and without test panel 5 (top). The puncture element 4 is a lancet 40, whose flat lancet body 41 tapers to a tip 42 at one end. A capillary structure 44 comprises a capillary channel 43 and a cell-type structure having capillary action, e.g., a matrix structure 24 or a cell structure. A capillary channel 43 extends from the tip 42 in the direction of the lancet body 41 to a liquid transfer area 35, in which a matrix structure 24, which is part of the capillary structure 44, is positioned. In FIG. 6c, the capillary channel 43 also extends beyond the liquid transfer area 35. A test panel 5, which consists of a support layer 45 and a test layer 47, is positioned adjacent to the matrix structure 24. The test panel 5 does not have a separate liquid retention structure.

Due to the optically homogeneous distribution of a liquid, the test element 3 is particularly suitable for a photometric measurement of a characteristic measuring variable. The support layer 45 is transparent, so that the test panel 5 can be optically registered by a lens 8a (compare FIG. 6c) and evaluated. Since the matrix structure 24 spreads out the liquid, a conventional cost-effective lens can be used for the photometric measurement, which focuses at 50 μm, for example. Production and mounting tolerances which have an effect on the relative position between lens 8a and its illuminated spot 51 to the test layer 47, do not play a role, since is they are greater than the illuminated spot 51 (optical evaluation area).

FIG. 6c shows an embodiment of the test element 3, in which the test panel 46 is positioned on the side of the lancet 40 opposite to the capillary channel 43. The matrix structure 24 is positioned parallel to the capillary channel 43 in the liquid transfer area 35, which is not located directly at the end of the capillary channel 43. In contrast thereto, in the exemplary embodiment according to FIG. 6b, the matrix structure 24 is positioned at the end of the capillary channel 43. In both cases, the planar matrix structure 24 is integrally connected to the lancet 40. It is preferably produced by etching in the same work step as the lancet 40.

Figure 7A:
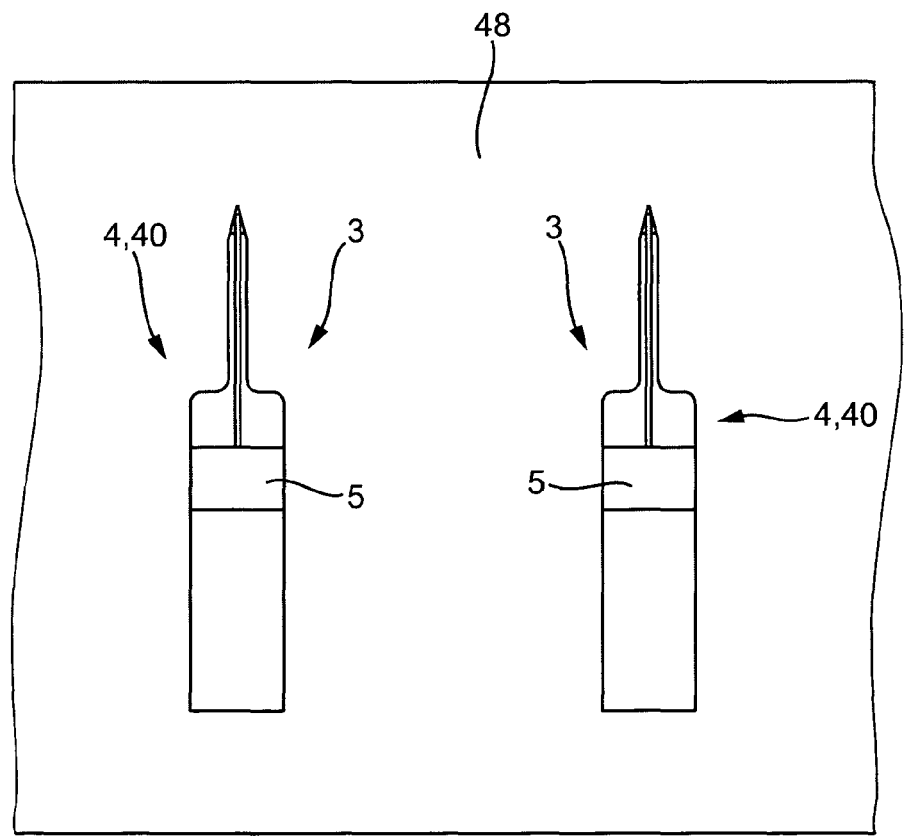
FIGS. 7a, b show a schematic outline of a test element positioned on a strip film.
Figure 7B:
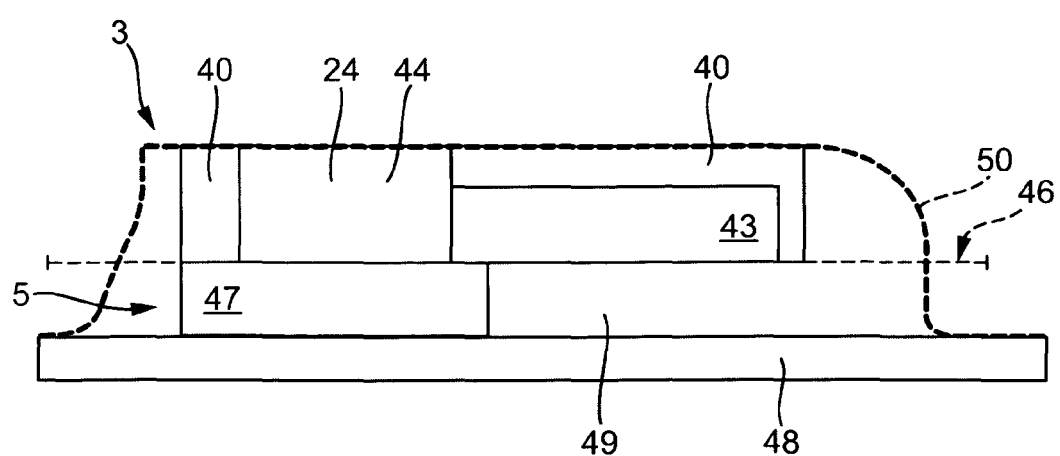

FIGS. 7a and 7b show the test element 3 from FIG. 6a having puncture element 4 (lancet 40) and test panel 5, which is implemented as a "lancet on tape". The support layer 45 of the test panel 5 is implemented as a strip film 48, on which multiple test elements 3 are positioned at a predefined spacing. The test elements 3 are glued onto the lower side of the transparent strip film 48. The adhesive surface advantageously adjoins the test panel 46. Adhesive substances can also be integrated in the test layer 47.

FIG. 7b shows a section through the test element 3 positioned on the strip film 48. The strip film 48 forms the support layer of the test panel 5. The lancet 40 contacts the test panel on a test panel plane 46 in such a manner that the liquid entry side 29 adjoins the transfer side 28 of the matrix structure 24. The lancet 40 is only connected to the strip film 48 over the test layer 47, alternatively additionally over an adhesive surface. A free space 49 is formed between the lancet 40 (having its capillary channel 43) and the strip film 48, in which excess body fluid can be collected.

Since the largest part of the lancet body 41, in particular the tapered part of the lancet body 41 having the capillary channel 43 and the tip, is not fastened on the strip film 48, to pierce the lancet 40 into a body part, the strip film 48 can be folded or angled (downward) relative to the lancet 40, so that the tip 42 can pierce into the body part, without the piercing being negatively influenced by the strip film 48.

For reasons of maintaining sterility during the storage, the individual test elements 3 on the strip film 48 can be covered using a sterile protective film 50. The film 50 can be stretched either over partial areas or the entire strip film 48. The strip film 48 having a plurality of test elements 3 can be stored in a magazine or a cassette, in particular rolled up in a cassette. A liquid retention structure (matrix structure 24) does not detach from the test panel 5 even if it is wound is up at a small radius.

Figure 8:
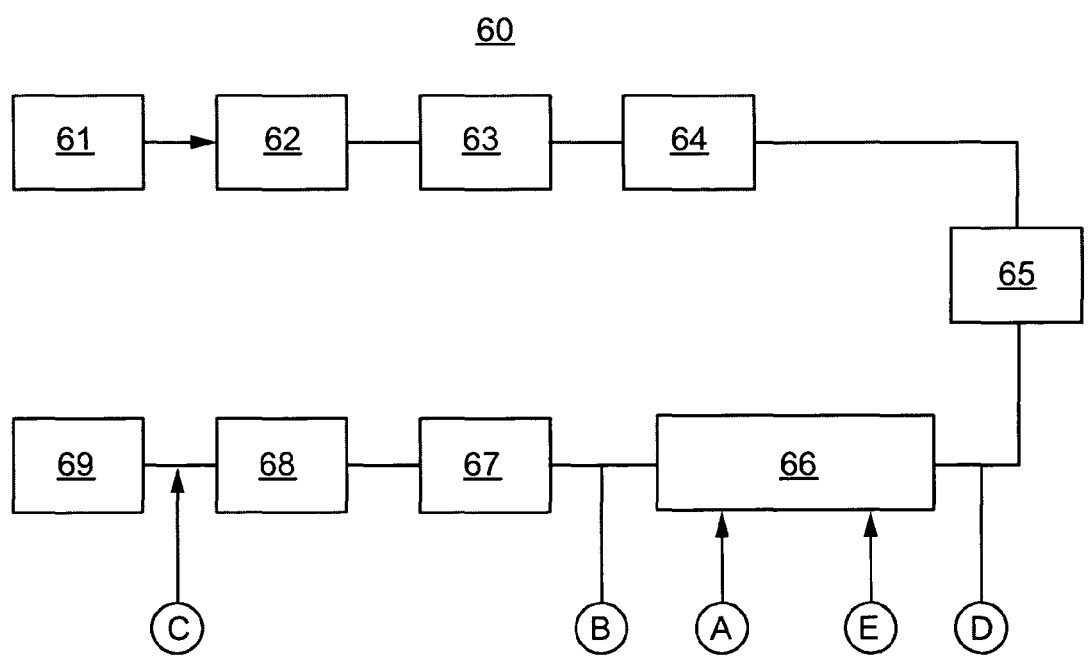
FIG. 8 shows a schematic outline of a production plant for producing a puncture element.

FIG. 8 schematically shows a production plant 60 for producing a puncture element 4 according to the invention having a capillary channel 15 and a capillary structure 13, as described above. A plurality of puncture elements 4 can be produced in mass production in an endless method on a metal strip using the plant 60. A thin metal strip is wound on an unwinding unit 61, which is cleaned in a cleaning facility 62 after it is unwound. The metal strip is preferably provided on both sides with the light-sensitive layer, for example, with a liquid or solid photoresist, in a coating unit 63. A mask in the form of the contour of the puncture element to be produced is applied to the metal strip in a printer unit 64. The metal strip is finally exposed. The coated and exposed metal strip is developed in a developer unit 65. The areas covered by the mask are washed free. In a next method step, the uncoated surfaces are etched, etched away, or etched through in an etching unit 66. At least the puncture element 4 having tip and the capillary channel 15 are generated here.

Subsequently, in a de-coating unit 67, the etching-resistant coating is removed and the metal strip is cleaned. After the drying in a dryer 68, it is wound onto a roll again in a winding unit 69. Alternatively, the individual puncture elements 4 could also be cut out of the strip. Alternatively, the metal strip having the puncture elements can also be connected to a carrier film or strip film, which forms the support layer of the test elements, and a test layer coated thereon, so that a band having test element according to the invention results, which can be separated and/or stored in magazines in a further method step.

In a preferred embodiment of the production method, not only the capillary channel 15 and the contour of the puncture element 4 are etched in the etching unit 66, but rather also the planar matrix structure 24 is also produced in the same etching procedure. With the aid of photochemical fine etching it is possible to produce the matrix structure 24 having a plurality of cells 25, the largest dimension of the cells 25 being between 30 μm and 100 μm. The height of the cells, which corresponds to the thickness of the metal strip, is preferably between 45 μm and 100 μm.

In an embodiment of the production method which is also preferred, the two-dimensional matrix structure 24 can be produced by lasers after the etching procedure, in which the puncture element 4 having the capillary channel 15 is produced. A laser unit having a laser, for example, an excimer laser, is used for this purpose.

The laser unit is preferably positioned at the points B and C shown in FIG. 8. The positioning at the point C has the advantage that the different methods of etching and laser cutting are spatially separated. Any influence of etching agent on the laser cut structure is prevented. Since the cleaned metal strip having the puncture elements is laser cut, no flue gases from another material, such as photoresist, arise during the laser cutting.

In an embodiment which is also preferred, the laser cutting is performed before the etching procedure. Preferred positions of the laser unit are shown at the points D and E in FIG. 8. The already laser cut structure is deburred during the etching.

The laser unit can alternatively be positioned at the point identified by A in FIG. 8. The laser cutting is performed between two etching procedures, in particular before the last etching procedure. In this laser position, the laser cut structures are deburred by the brief influence of the etching agent, without impermissibly changing or distorting the structures, however.

The invention claimed is:

1. Test element for generating a puncture wound in a body part, for receiving a body fluid sample from the body part, and for analyzing by means of a reagent system, whose reaction with an analyte contained in the body fluid results in an optically measurable change of a measuring variable, which is characteristic for the desired analytical result, on the test element, comprising a puncture element and a test panel, which contains at least a part of the reagent system, wherein the puncture element has a tip positioned at one end of the puncture element for generating a wound in the body part and a capillary structure, which is implemented so that after the tip of the puncture element pierces into the skin, body fluid penetrates into the capillary structure, the puncture element and the test panel can be positioned relative to one another in a liquid transfer position so that the test panel is in fluid contact with a part of the capillary structure of the puncture element, body fluid which has penetrated into the capillary structure being able to be transferred to the test panel, the test panel comprises a transparent support layer and a test layer, wherein the test layer is coated on the surface of the transparent support layer, wherein the transparent support layer is non-porous, wherein the side of the test layer facing away from the support layer forming the liquid entry side, which faces toward the capillary structure in the liquid transfer position, in the liquid transfer position, the liquid entry side of the test layer directly adjoins the capillary structure in such a manner that a direct liquid transfer occurs from the capillary structure into the test layer, and wherein the test layer comprises two partial layers, a first partial layer coated on the support layer being a reaction layer and a second partial layer being an opaque light blocking layer coated on the first partial layer.

2. Test element according to claim 1, characterized in that the test panel is fixed on the puncture element, so that the puncture element and the test panel are permanently in fluid contact.

3. Test element according to claim 1, characterized in that both the reaction layer and also the opaque light blocking layer contain an enzyme and a coloration reagent (indicator), the quantity of the enzyme in the reaction layer being greater than that in the light blocking layer and the quantity of the indicator in the reaction layer being less than that in the light blocking layer.

4. Test element according to claim 1, characterized in that at least one component of the reagent system, preferably an enzyme, is bound to another component of the test layer, in particular to a filler contained in the test layer.

5. Test element according to claim 1, characterized in that the capillary structure includes a two-dimensional matrix structure having a plurality of cells having cell cavities and a capillary channel, through which body fluid is transported to the two-dimensional matrix structure after the piercing of the tip of the puncture element into the skin, wherein the largest dimension of the cell cavities of the two-dimensional matrix structure being less than the average width of the capillary channel, the cell cavities having a defined height perpendicularly to the two-dimensional extension of the matrix structure, by which the minimum value of the layer thickness of the liquid layer is ensured, and the cells being open on a transfer side of the matrix structure, which adjoins the liquid entry side of the test panel.

6. Test element according to claim 5, characterized in that the two-dimensional matrix structure is positioned parallel and adjacent to a partial length of the capillary channel, and the cells of the matrix structure have cell openings on a liquid entry side, which faces toward the capillary channel and is opposite to the transfer side, so that the liquid penetrates through these cell openings into the cell cavities of the matrix structure.

7. Test element according to claim 5, characterized in that the matrix structure comprises at least 20, preferably at least 25, particularly preferably at least 50, and still more preferably at least 100 cells.

8. Test element according to claim 5, characterized in that the thickness of the test layer is at most 20 μm.

9. Test element according to claim 5, characterized in that the matrix structure is implemented integrally with the puncture element.

10. Test element according to claim 5, characterized in that the cell cavities of the matrix structure widen toward the transfer side, preferably widen continuously.

11. Test element according to claim 5, characterized in that the capillary channel and the matrix structure are produced in a common production method step by etching or by etching and laser cutting.

12. Analysis system for analyzing a body fluid from a body part comprising a test element according to claim 1 and an analysis device having a housing, a coupling mechanism for coupling the test element to a drive mechanism of the analysis device, to move it on a movement path of a piercing movement, and a measuring and evaluation unit for measuring a change of a reagent which reacts with the body fluid, in order to analyze an analyte in the body fluid.

\* \* \* \* \*

UNITED STATES PATENT AND TRADEMARK OFFICE
CERTIFICATE OF CORRECTION

PATENT NO. : 9,089,293 B2  
APPLICATION NO. : 13/351496  
DATED : July 28, 2015  
INVENTOR(S) : Haar et al.

Page 1 of 1

It is certified that error appears in the above-identified patent and that said Letters Patent is hereby corrected as shown below:

In the specification
Col. 1, line 23, replace "They is are common" with --They are common--
Col. 2, line 3, replace "first brought is" with --first brought--
Col. 2, line 51, replace "to one is" with --to one--
Col. 3, line 33, replace "matrix is structure" with --matrix structure--
Col. 4, line 15, replace "consists of is multiple" with --consists of multiple--
Col. 4, line 63, replace "is layer type" with --layer type--
Col. 5, line 44, replace "The reagent is system" with --The reagent system--
Col. 6, line 25, replace "optical is measurement" with --optical measurement--
Col. 7, line 3, replace "after the is penetration" with --after the penetration--
Col. 7, line 52, replace "the electrode is" with --the electrode--
Col. 8, line 33, replace "ensured to is achieve" with --ensured to achieve--
Col. 9, line 11, replace "On is the one hand" with --On the one hand--
Col. 9, line 55, replace "is such a manner" with --such a manner--
Col. 10, line 35, replace "A liquid is transferred" with --A liquid transferred--
Col. 14, line 22, replace "beyond is this section" with --beyond this section--
Col. 15, line 3, replace "liquid is layer" with --liquid layer--
Col. 15, line 48, replace "of a is metal structure" with --of a metal structure--
Col. 16, line 15, replace "50 mL" with --50 nL--
Col. 16, line 20, replace "0.096 mL" with --0.096 nL--
Col. 16, line 21, replace "7.7 mL" with --7.7 nL--
Col. 16, line 23, replace "4.5 mL" with --4.5 nL--
Col. 16, line 26, replace "adjoining is test" with --adjoining test--
Col. 17, line 7, replace "since is they are" with --since they are--
Col. 17, line 53, replace "it is wound is up" with --it is wound up--

Signed and Sealed this  
Second Day of February, 2016

Michelle K. Lee  
*Director of the United States Patent and Trademark Office*